United States Patent [19]
Grant et al.

[11] Patent Number: 5,260,417
[45] Date of Patent: Nov. 9, 1993

[54] MEGAKARYOCYTE GROWTH PROMOTING ACTIVITY PROTEIN

[75] Inventors: Barbara W. Grant; Kenneth G. Mann, both of Shelburne, Vt.

[73] Assignees: Genetics Institute, Inc., Cambridge, Mass.; University of Vermont and State Agricultural College, Burlington, Vt.

[21] Appl. No.: 761,906

[22] PCT Filed: Apr. 2, 1990

[86] PCT No.: PCT/US90/01725
§ 371 Date: Sep. 12, 1991
§ 102(e) Date: Sep. 12, 1991

[87] PCT Pub. No.: WO90/12108
PCT Pub. Date: Oct. 18, 1990

Related U.S. Application Data

[63] Continuation-in-part of Ser. No. 332,651, Apr. 3, 1989, abandoned.

[51] Int. Cl.$^5$ .................. C07K 15/00; C07K 15/06
[52] U.S. Cl. .................. 530/351; 424/85.1; 530/399
[58] Field of Search .......... 530/351, 399; 424/85.1; 514/12

[56] References Cited

U.S. PATENT DOCUMENTS

| | | | |
|---|---|---|---|
| 4,658,018 | 4/1987 | Urdal et al. | 530/351 |
| 4,695,542 | 9/1987 | Yokota et al. | 435/68 |
| 4,894,440 | 1/1990 | Rosenberg | 530/351 |
| 5,032,396 | 7/1991 | Williams | 424/85.2 |

FOREIGN PATENT DOCUMENTS

| | | |
|---|---|---|
| 598297B2 | 6/1990 | Australia . |
| 0260918 | 3/1988 | European Pat. Off. . |
| 354989 | 2/1990 | European Pat. Off. . |
| 89111714.5 | 2/1990 | European Pat. Off. . |
| 62-223126 | 3/1986 | Japan . |
| WO90/03397 | 4/1990 | PCT Int'l Appl. . |
| WO91/18925 | 12/1991 | PCT Int'l Appl. . |
| WO92/00319 | 1/1992 | PCT Int'l Appl. . |

OTHER PUBLICATIONS

Hoffman et al. *J. Clin Invest* 75:1174–1182 (1985).
Kawakita et al. *Br. J. Haem* 62:715–722 (1986).
Kawakita et al *Blood* 61:556–560 (1983).
Yang et al., Chem. Abstr. 105(5):36292x (1986).
Kawakita et al., Chem. Abstr. 105(13):109405y (1986).
Miyake et al., Chem. Abstr. 98(11):83667v (1982).
Kawakita et al., Prog. Clin. Biol. Res. 215:201–208 (1986).
Hoffman et al., Blood Cells 13:75–86 (1987).
DeAlarcon, Blood Cells 15:173–185 (1989).
Bagnara et al., Exp. Hematol 15:679–684 (1987).
Langley et al., Exp. Hematol 18:615 (1990).
Dexter, Colony Stimulating Factors: 215–229 (1990).
Evatt et al., Megakaryocyte Biology and Precursors:-59–75 (1981).
DeAlarcon, Blood Cells 15:186–191 (1989).
McDonald, International Journal of Cell Colony 7:139–153 (1989).
Kuriya et al., Blood Cell 12:233–247 (1986).
Choudhury et al., J. Lab. Clin. Med. 134:382–388 (1989).
Lu et al., Behring Inst. Mitt 83:181–187 (1988).
Bruno et al., Exp. Hematol. 16:371–377 (1988).
Bruno et al., Exp. Hematol. 17:1038–1043 (1989).
Ishibashi et al., Blood 74(4):1241–1244 (1989).
Hoffman, Blood 74:1196–1212 (1989).
Greenberg, J. of Biol. Chem. 262:3269–3277 (1987).
Yang et al., J. Clin. Invest. 77(6):1873–1880 (1986).
Miyake et al., Stem Cells 2(3):129–144 (1982).

(List continued on next page.)

*Primary Examiner*—Robert J. Hill, Jr.
*Assistant Examiner*—Shelly G. Cermak
*Attorney, Agent, or Firm*—M. C. Meinert; Thomas DesRosier; Bruce Eisen

[57] ABSTRACT

A novel human megakaryocytopoietic growth promoting activity factor capable of stimulating the growth of megakaryocytes and augments the differentiation or maturation of megakaryocytes. Also provided are processes for obtaining the factor in homogeneous form and producing it by recombinant genetic engineering techniques.

8 Claims, No Drawings

OTHER PUBLICATIONS

Hunt et al., Blood 76(10):460A, abstract #1830 (1990).
Shimizu et al., Experimental Hematology 14(6):490 (1986).
Shimizu, Experimental Hematology 15(5):492 (1987).
Mazur et al., Experimental Hematology 13(11):1164–1172 (1985).
Clark et al., Science 236:1229–1237 (1987).
Williams et al., J. Cell. Phys. 110:101–104 (1982).
Burstein et al., J. Cell. Phys. 109:333–341 (1981).
Grant et al., Blood 69:1334–1339 (1987).
Tayrien et al., J. Biol. Chem. 262:3262–3268 (1987).
Enomoto et al., Br. J. Haemat. 45:551–556 (1980).
Kuriya et al., Exp. Cell. Biol. 55:257–264 (1987).
McDonald, Exp. Hematol. 16:201–205 (1988).
Gewirtz, Seminars in Hematology 23:27–42 (1986).
Straneva, Exp. Hematol. 14:919–929 (1986).
Grant et al., Blood 70 Supl. 1 (1987).
Grant et al., Clin. Res. 37:380a (1989).
Mazur, Exp, Hematol. 15:340–350 (1987).
Ishibashi et al., J. Clin. Invest. 79:286–289 (1987).
Ishibashi et al., Proc. Natl. Acad. Sci. U.S.A. 86:5953–5957 (1989).
Teramura et al., Exp. Hematol. 17:1011–1016 (1989).
Long et al., J. Clin. Invest. 82:1779–1786 (1988).
Hill et al., Exp. Hematol. 14:752–759 (1986).
Straneva et al., Exp. Hematol. 15:657–663 (1987).
McDonald et al., Biochem. Med. Metab. Biol. 37:335–343 (1987).
Kawakita et al., British J. of Haem. 48:609–615 (1981).

MEGAKARYOCYTE GROWTH PROMOTING ACTIVITY PROTEIN

This is a continuation-in-part of pending U.S. patent application Ser. No. 07/332,651, filed on Apr. 3, 1989, now abandoned.

The present invention relates to a novel protein factor which stimulates the growth of megakaryocytes and augments the differentiation or maturation of megakaryocytes. Also provided are processes for obtaining the factor in homogeneous form and producing it by recombinant genetic engineering techniques.

BACKGROUND OF THE INVENTION

Megakaryocytes are the hematopoietic cells, largely found in the bone marrow, but also in peripheral blood and perhaps other tissues as well, which produce platelets (also known as thrombocytes) and subsequently release them into circulation. Megakaryocytes, like all of the hematopoietic cells of the human hematopoietic system, ultimately derive from a primitive pluripotent marrow stem cell after passing through a complex pathway comprising many cellular divisions and considerable differentiation and maturation. Mature megakaryocytes ultimately undergo subdivisions and release the cytoplasmic fragments which are circulating platelets.

The platelets derived from these megakaryocytic cells are critical for initiating blood clot formation at the site of injury Platelets also release growth factors at the site of clot formation that speed the process of wound healing and may serve other functions. Clinical experience has shown that control mechanisms exist to maintain effective platelet numbers in humans, but that at times these specific controls are either inadequate or ineffective and lead to depressed levels of platelets (thrombocytopenia) or thrombocytosis despite normal numbers of red blood cells and white blood cells.

The inability to form clots is the most immediate and serious consequence of a low platelet count, a potentially fatal complication of many therapies for cancer. Such cancer patients are generally treated for this problem with platelet transfusions. Other patients frequently requiring platelet transfusions are those undergoing bone marrow transplantation or patients with aplastic anemia.

Platelets for such procedures are obtained by plateletphoresis from normal donors Like most human blood products, platelets for transfusion have a relatively short shelf-life and also expose the patients to considerable risk of exposure to dangerous viruses, such as the human immunodeficiency virus (HIV) or the various hepatitis viruses.

The ability to stimulate endogenous platelet formation in thrombocytopenic patients with a concomitant reduction in their dependence on platelet transfusion would be of great benefit. In addition the ability to correct or prevent thrombocytopenia in patients undergoing radiation therapy or chemotherapy for cancer would make such treatments safer and possibly permit increases in the intensity of the therapy thereby yielding greater anti-cancer effects.

For these reasons considerable research has been devoted to the identification and purification of factors involved in the regulation of megakaryocyte and platelet production. Although there is considerable controversy, the factors regulating the growth and differentiation of hematopoietic cells into mature megakaryocyte cells and the subsequent production of platelets by these cells are believed to fall into two classes.

Megakaryocyte colony-stimulating factors (meg-CSFs) are the first group of regulatory factors which function to support the proliferation and differentiation of megakaryocytic progenitors (CFU-M) in culture. The second group of factors have been defined by their activity towards megakaryocytes in either in vivo or in vitro bioassays. Factors which elicit an in vivo response, such as an increase in the circulating level of platelets have been defined as thrombopoietin ("TPO"). Factors which support either the differentiation, maturation or development of megakaryocytes in an in vitro culture system have been termed megakaryocyte stimulating activity, megakaryocyte potentiating activity, or thrombopoietin-like activity. It is unclear whether thrombopoietic factors are structurally identical or related to any of the in vitro defined megakaryocyte stimulating activities.

From the studies reported to date, it is not clear whether activities identified as meg-CSF also have TPO activity or vice versa. Many different reports in the literature describe factors which interact with cells of the megakaryocytic lineage and report megakaryocyte growth promoting activities specific for the megakaryocyte lineage. [See, e.g., E. Mazur, *Exp. Hematol.*, 15:340-350 (1987); N. Williams et al, *J. Cell. Physiol.*, 110:101-104 (1982); J. E. Straneva et al, *Exp. Hematol.*, 14:919-929 (1986)]. An understanding of the specifics of positive and negative control of megakaryocytopoiesis is incomplete.

For example, human IL-3 supports human megakaryocyte colony formation and, at least in monkeys, also frequently elicits an elevation in platelet count. However, IL-3 influences hematopoietic cell development in all of the hematopoietic lineages and can be distinguished from specific regulators of megakaryocytopoiesis and platelet formation which interact selectively with cells of the megakaryocytic lineage.

There is strong evidence that in mice, murine IL-6 has thrombopoietin activity in vivo and augments murine megakaryocyte colony formation with IL-3 in in vitro bioassays. However the thrombopoietic effect is not striking (50-60% increase in circulating platelet numbers in 5 days) [T. Ishibashi et al, *J. Clin. Invest.*, 79:286-289 (1987); T. Ishibashi et al, *Blood*, 74(4):1241-1244 (1989); T. Ishibashi et al, *Proc. Natl. Acad. Sci. USA*, 86:5953-5957 (1989)]. In vivo administration of IL-6 to mice also increases megakaryocyte size and ploidy. There is much less evidence that IL-6 has TPO-like or megakaryocyte potentiating activity in human in vitro assays [see, e.g., E. Bruno and R. Hoffman, *Exp. Hematol.*, 17:1038-4 (1989)]. In most of these assays human IL-6 has shown no TPO-like activity [M. Teramura et al, *Exp. Hematol.*, 17:1011-1016 (1989) and M. W. Long et al, *J. Clin. Invest.*, 82:1779-1786 (1988)].

R. Hoffman et al, *J. Clin. Invest.*, 75:1174-1182 (1985) describes using a human megakaryocyte colony assay to purify from serum a colony stimulating activity with an apparent MW of 46,000. This factor is found in the 70-80% ammonium sulfate cut, binds to wheat germ lectin, and loses activity after deglycosylation. A similar activity was detected in thrombocytopenic rabbit plasma that increases the incorporation of $^{75}$Se methionine into platelets in mice. This activity was purified 7,000 fold from plasma, but contaminating proteins were present as determined by SDS-PAGE electrophoresis. See, e.g., R. Hill and J. Levin, *Exp. Hematol.*, 14:752-759 (1986). Other serum derived factors are described by J. E. Straneva et al, *Exp. Hematol.,* 15:657-663 (1987); and E. Mazur et al, *Exp. Hematol.,* 13:1164-1172 (1985].

Megakaryocyte growth promoting activities, and thrombopoietin also have been derived from human embryonic kidney (HEK) cells [See, e.g., T. P. McDonald, *Exp. Hematol.,* 16:201-205 (1988); T. P. McDonald et al, *Biochem. Med. Metab. Biol.,* 37:335-343 (1987); G. Tayrien and R. D. Rosenberg, *J. Biol. Chem.,* 262:3262-3268 (1987) and others]. Each has purified to homogeneity a 15,000 molecular weight activity that readily dimerizes to 30,000 molecular weight HEK-derived activity can increase isotopic incorporation into platelets when given parenterally in mice, and increase the production of platelet factor 4-like proteins in rodent megakaryocyte lineage cells. This activity is heat stable, and maintains activity after treatment with endoglycosidases, and binds to wheat germ lectin.

Finally, activities have been described from urine that promote megakaryocyte growth in rodents in vivo and in marrow culture. Kawakita has partially purified an activity from urine that varies with patient platelet count, and under dissociating conditions has a molecular weight of 45,000. The activity of this on human megakaryocyte progenitors has not been tested, nor has it been shown to be specific for the megakaryocyte hematopoietic lineage. [M. Kawakita et al, *Br. J. Haem.,* 62:715-722 (1986); M. Kawakita et al, *Blood,* 61:556-560 (1983); see, also, S. Kuriya et al, *Exp. Cell Biol.,* 55:257-264 (1987); K. Enomoto et al, *Brit. J. Haem.,* 45:551-556 (1980)].

Despite such reports tentatively identifying such regulatory factors, the biochemical and biological identification and characterization of these factors has been hampered by the small quantities of the naturally occurring factors available from natural sources, e.g., blood and urine.

There remains a need in the art for the isolation, identification and production of additional proteins purified from their natural sources or otherwise produced in homogeneous form, which are capable of stimulating or enhancing the production of platelets in vivo, to replace presently employed platelet transfusions and otherwise useful in the treatment and/or diagnosis of blood and blood platelet disorders.

BRIEF SUMMARY OF THE INVENTION

In one aspect the present invention provides a novel proteinaceous megakaryocyte growth promoting activity factor ("MGPA") which is substantially free from other human proteins. This protein may be purified from cell sources producing the factor naturally or upon induction with other factors. It may also be produced by recombinant genetic engineering techniques. MGPA may also be synthesized by chemical techniques, or a combination of the above-listed techniques.

The MGPA of the present invention has been found to be specific to the megakaryocyte lineage, augmenting maturation and/or proliferation of megakaryocytes in the assay of Example 1 below.

Active MGPA has an apparent molecular weight of approximately 45 kd as determined by gel filtration chromatography and sodium dodecyl sulfate polyacrylamide gel electrophoresis. MGPA is further characterized in that it does not bind wheat germ lectin. The factor does bind to a cation exchange resin (e.g., Pharmacia Mono S column) at acidic pH, but does not bind to an anion exchange resin at neutral pH. MGPA is found consistently in the 30-50% ammonium sulphate precipitate of thrombocytopenic patient plasma, but cannot be detected in normal human plasma. MGPA is present in normal urinary protein concentrates.

MGPA is further characterized by its ability to act in an additive or synergistic manner with GMCSF and IL3 to promote megakaryocyte growth in liquid bone marrow culture systems.

Still a further aspect of the present invention is a process for isolating and purifying the MGPA composition of the present invention or a fragment thereof from human urine. This purification process provided by the present invention involves the following steps. The first two steps are ammonium sulfate precipitation, followed by cation exchange column chromatography on sulphopropyl Sephadex at pH5.4 in 25 mM ammonium acetate buffer. This step is followed by subjecting the MGPA-containing fractions to filtration through a polyethyleneimine anion exchange membrane in 50 mM ammonium bicarbonate buffer at pH 7.4. The MGPA-containing filtrate is then subjected to reverse phase high performance liquid chromatography (HPLC) on a C3 column with 0.05% trifluoroacetic acid (TFA) and acetonitrile as the mobile phase solvent.

A further aspect of the present invention is homogeneous MGPA purified from urine or produced via recombinant or synthetic techniques which is characterized by a specific activity in the radioimmunoassay of greater than $1 \times 10^6$ units/mg.

Another aspect of the present invention is a DNA sequence that encodes the expression of a human MGPA protein. This DNA sequence may include an isolated DNA sequence that encodes the expression of a human MGPA protein as described above. The DNA sequence may also include 5' and 3' human non-coding sequences flanking the MGPA coding sequence. The DNA sequence may also encode an amino terminal signal peptide.

Also provided by the present invention is a recombinant DNA molecule comprising vector DNA and a DNA sequence encoding human MGPA. The DNA molecule provides the MGPA DNA in operative association with a regulatory sequence capable of directing the replication and expression of MGPA in a selected host cell. Host cells transformed with such DNA molecules for use in expressing recombinant MGPA protein are also provided by the present invention.

The DNA molecules and transformed cells of the invention are employed in another aspect, a novel process for producing recombinant human MGPA protein, or peptide fragments thereof. In this process a cell line transformed with a DNA sequence encoding expression of MGPA protein or a fragment thereof (or a recombinant DNA molecule as described above) in operative association with a suitable regulatory or expression control sequence capable of controlling expression of the protein is cultured under appropriate conditions permitting expression of the recombinant DNA. This claimed process may employ a number of known cells as host cells for expression of the protein. Presently preferred cell lines for producing MGPA are mammalian cell lines and bacterial cells.

The expressed MGPA protein is then harvested from the host cell, cell lysate or culture medium by suitable conventional means. The conditioned medium may be processed through the same purification steps or modifications thereof as used to isolate the MGPA from urine.

As still a further aspect of the present invention, there is provided recombinant MGPA protein. This protein is substantially free from other human proteinaceous materials and comprising a DNA sequence encoding one or more of the peptide fragments or sequences described herein. The MGPA protein of this invention is also characterized by containing one or more of the physical, biochemical, pharmacological or biological activities described herein.

Another aspect of this invention provides pharmaceutical compositions containing a therapeutically effective amount of homogeneous or recombinant MGPA or an effective amount of one or more active peptide fragments thereof. These pharmaceutical compositions may be employed in methods for treating disease states or disorders characterized by a deficiency or defect of platelets.

Thus the MGPA composition of the present invention or pharmaceutically effective fragments thereof may be employed in the treatment of aplastic anemias, e.g., to augment production of platelets in patients having impaired platelet production (such as AIDS patients or patients undergoing cancer chemotherapy). The MGPA may be used to treat blood disorders such as thrombocytopenia. MGPA may be used as an adjunctive therapy for bone marrow transplant patients.

A further aspect of the invention, therefore, is a method for treating these and other pathological states resulting from a deficiency of platelets by administering to a patient a therapeutically effective amount of MGPA or one or more peptide fragments thereof in a suitable pharmaceutical carrier. These therapeutic methods may include administering simultaneously or sequentially with MGPA or one or more peptide fragments thereof an effective amount of at least one other meg-CSF or TPO-like factor, a cytokine, hematopoietin, interleukin, growth factor, or antibody.

Still another aspect of the present invention are antibodies directed against human MGPA or a fragment thereof. As part of this aspect, therefore, the invention claims cell lines capable of secreting such antibodies and methods for their production and use in diagnostic or therapeutic procedures.

Other aspects and advantages of the present invention will be apparent upon consideration of the following detailed description of preferred embodiments thereof.

DETAILED DESCRIPTION OF THE INVENTION

The novel human megakaryocyte growth promoting activity factor, MGPA, provided by the present invention is a homogeneous protein or proteinaceous composition substantially free of association with other human proteinaceous materials. This protein can be produced via recombinant techniques to enable large quantity production of pure, active MGPA useful for therapeutic applications. Alternatively this protein may be obtained as a homogeneous protein purified from human urine or from a mammalian cell line secreting or expressing it. Further MGPA or active fragments thereof may be chemically synthesized.

MGPA of the present invention is characterized by one or more of the following biochemical and biological properties:

(1) The composition of the present invention has an apparent molecular weight of approximately 45 kd as determined by 8% sodium dodecyl sulfate polyacrylamide gel electrophoresis (SDS-PAGE) under either non-reducing or reducing conditions.

(2) The composition of the present invention has an apparent molecular weight of approximately 40-50 kd on gel filtration chromatography.

(3) The composition of the present invention has a specific activity in the megakaryocyte growth promoting assay of Example 1 of greater than approximately $1 \times 10^6$ units/mg protein.

(4) The MGPA composition of the present invention is capable of binding a cation exchange column under acidic conditions of pH 5.4.

(5) The MGPA composition of the present invention is not capable of binding to Wheat Germ lectin.

(6) The MGPA composition of the present invention does not bind to an anion exchange resin at neutral pH.

(7) The MGPA composition of the present invention is found consistently in the 30–50% ammonium sulfate precipitate of thrombocytic patient urine.

(8) The MGPA composition of the present invention cannot be detected in normal human plasma with the current assays.

The biological activity of the MGPA composition of the present invention is demonstrated by its ability to stimulate the growth and development of megakaryocytes in the radioimmunological megakaryocyte growth promoting assay of Example 1. This in vitro assay for regulatory activities stimulated by low platelet counts detects cell-bound GPIIb/IIIa, a megakaryocyte lineage specific glycoprotein which is expressed on small morphologically unrecognizable megakaryocyte precursors as well as recognizable megakaryocytes and platelets. The assay enables quantitative assessment of in vitro megakaryocytopoiesis [B. W. Grant et al, *Blood*, 69:1334–1339 (1987)]. This assay is described in detail in Example 1 below.

MGPA was originally detected in the citrated plasma of human patients with aplastic anemia. Unfractionated plasma from these patients demonstrate an enhanced support of megakaryocyte growth in vitro. Plasmas from other thrombocytopenic patients have been shown to contain MGPA. Human MGPA was initially purified from this human plasma by a sequence of purification steps and techniques specifically described in Example 2 below. However, this factor may also be purified from thrombocytopenic patient urine.

Two cellular sources of MGPA have presently been identified. Osteosarcoma cells explanted from a tumor and passaged in culture, called HS10, elaborate MGPA. MGPA has not been detected in conditioned media when HS10 cells are grown in the presence of serum. When without serum, these cells produce an activity very similar to the plasma MGPA with an unfractionated conditioned medium having 100 to 200 units MGPA per $A_{280}$ unit. This activity co-purifies with the plasma MGPA on an ACA34 gel filtration column. Because HS10 is not a transformed cell line, it grows slowly, dies off, and secretes very little MGPA (serum free conditioned media has about 1/10 of a unit per milliliter). These cells may be transformed to produce MGPA consistently. Alternatively, other osteosarcoma cell lines may be detected with similar MGPA production.

MGPA similar to that found in plasma has also been detected in conditioned media from human umbilical vein endothelial (HUV) cells. Conditioned media from these cells (supplied by Dr. Faller, Dana-Farber and Dr. Shorer, University of Minnesota) have been found to promote megakaryocyte growth in the radioimmunoassay of Example 1. This material co-purifies with plasma MGPA by gel filtration, and supports megakaryocyte growth in phytohemagglutinin-leukocyte conditioned medium (PHALCM), IL3 or GM-CSF in a dose dependent way similar to the plasma and urinary MGPA. This activity is not inhibited by anti GM-CSF.

The purification techniques employed in obtaining MGPA from human urine comprises the following steps which are outlined in detail in Example 3. These steps include subjecting the unconcentrated urine to ammonium sulfate precipitation; binding the 80% ammonium sulfate fraction to a cation exchange chromatographic column (sulfopropyl Sephadex) in 25 mM ammonium acetate, pH 5.4 and eluting the bound protein in a gradient of NaCl; passing the 0.15M NaCl eluate containing MGPA through an anion exchange membrane (polyethyleneimine) in ammonium bicarbonate buffer, pH 7.4; and finally applying the filtrate through a cycle of reverse phase HPLC using $H_2O$/TFA/acetonitrile as the solvent.

Fractionation techniques that have not been useful include hydroxyapatite, heparin sepharose and wheat germ agglutinin using two different lectin bead preparations [Sigma].

Homogeneous MGPA may be obtained by applying the above purification procedures, which are described in detail in Example 3, to human thrombocytopenic urine or other sources of human MGPA e.g., cell or tissue sources. Procedures for culturing a cell (or tissue) source which may be found to produce MGPA are known to those of skill in the art.

MGPA of this invention differs from other TPO-like factors of the prior art. For example, MGPA differs from TSF [MacDonald, supra] and megCSA [Hoffman, supra] in apparent molecular weight, in the % ammonium sulfate that precipitates it from plasma, in its behavior on ion exchange columns, and in its lack of binding to wheat germ lectin.

MGPA or one or more peptide fragments thereof may also be produced via recombinant techniques. To obtain the DNA sequence for MGPA, the purified MGPA material is reduced and digested with trypsin. Tryptic fragments are isolated and sequenced by conventional techniques. Oligonucleotide probes are synthesized using the genetic code to predict all possible sequences that encode the amino acid sequences of the tryptic fragments. Several sequences are generated as probes. The MGPA cDNA is identified by using these probes to screen a human genomic library. Alternatively, the mRNA from a cell source of MGPA can be used to make a cDNA library which can be screened with the probes to identify the cDNA encoding the MGPA polypeptide.

Using these probes to screen human genomic library, a cDNA clone is obtained. To obtain a full length clone, the obtained cDNA sequences may be employed as probes to rescreen the library and hybridize to the full length MGPA sequence.

The human CDNA for MGPA can also be obtained by subcloning a full length human genomic clone into an expression vector, transfecting it into COS cells, preparing a cDNA library from these transfected COS cells and screening by hybridization for MGPA cDNA. Once the entire cDNA is identified, it or any portion of it that encodes an active fragment of MGPA, can be introduced into any one of a variety of expression vectors to make an expression system for MGPA or one or more fragments thereof.

By such use of recombinant techniques, DNA sequences encoding the MGPA polypeptide are obtained. The present invention also encompasses these DNA sequences, free of association with DNA sequences encoding other proteins, and coding on expression for MGPA polypeptides. These DNA sequences include those sequences encoding all or a fragment of MGPA and those sequences which hybridize under stringent hybridization conditions [see, T. Maniatis et al, *Molecular Cloning (A Laboratory Manual)*. Cold Spring Harbor Laboratory (1982), pages 387 to 389] to the DNA sequences.

An example of one such stringent hybridization condition is hybridization in 4XSSC at 65° C., followed by a washing in 0.1XSSC at 65° C. for an hour. Alternatively an exemplary stringent hybridization condition is in 50% formamide, 4XSSC at 42° C.

DNA sequences which hybridize to the sequences for MGPA under relaxed hybridization conditions and which code on expression for MGPA peptides having MGPA biological properties also encode novel MGPA polypeptides. Examples of such non-stringent hybridization conditions are 4XSSC at 50° C. or hybridization with 30-40% formamide at 42° C. For example, a DNA sequence which shares regions of significant homology, e.g., sites of glycosylation or disulfide linkages, with the sequences of MGPA and encodes a protein having one or more MGPA biological properties clearly encodes a MGPA polypeptide even if such a DNA sequence would not stringently hybridize to the MGPA sequences.

Allelic variations (naturally-occurring base changes in the species population which may or may not result in an amino acid change) of DNA sequences encoding the peptide sequences of MGPA are also included in the present invention, as well as analogs or derivatives thereof. Similarly, DNA sequences which code for MGPA polypeptides but which differ in codon sequence due to the degeneracies of the genetic code or variations in the DNA sequence of MGPA which are caused by point mutations or by induced modifications to enhance the activity, half-life or production of the polypeptides encoded thereby are also encompassed in the invention.

MGPA polypeptides may also be produced by known conventional chemical synthesis. Methods for constructing the polypeptides of the present invention by synthetic means are known to those of skill in the art. The synthetically-constructed MGPA polypeptide sequences, by virtue of sharing primary, secondary, or tertiary structural and conformational characteristics with MGPA polypeptides may possess MGPA biological properties in common therewith. Thus, they may be employed as biologically active or immunological substitutes for natural, purified MGPA polypeptides in therapeutic and immunological processes.

Modifications in the peptides or DNA sequences encoding MGPA can be made by one skilled in the art using known techniques. Modifications of interest in the MGPA sequences may include the replacement, insertion or deletion of a selected amino acid residue in the coding sequences. Mutagenic techniques for such replacement, insertion or deletion are well known to one skilled in the art. [See, e.g., U.S. Pat. No. 4,518,584.]

Specific mutations of the sequences of the MGPA polypeptide may involve modifications of a glycosylation site, if any. The absence of glycosylation or only partial glycosylation results from amino acid substitution or deletion at any asparagine-linked glycosylation recognition site or at any site of the molecule that is modified by addition of O-linked carbohydrate. An asparagine-linked glycosylation recognition site comprises a tripeptide sequence which is specifically recognized by appropriate cellular glycosylation enzymes. These tripeptide sequences are either Asp-X-Thr or Asp-X-Ser, where X can be any amino acid. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences produces variants which are not glycosylated at that site.

Other analogs and derivatives of the sequence of MGPA which would be expected to retain MGPA activity in whole or in part may also be easily made by one of skill in the art given the disclosures herein. One such modification may be the attachment of polyethylene glycol (PEG) onto existing lysine residues in the MGPA sequence or the insertion of one or more lysine residues or other amino acid residues that can react with PEG or PEG derivatives into the sequence by conventional techniques to enable the attachment of PEG moieties. Such modifications are believed to be encompassed by this invention.

The present invention also provides a method for producing MGPA polypeptides or active fragments thereof. One method of the present invention involves introducing the cDNA encoding a MGPA polypeptide into an expression vector to make an expression system for MGPA. A selected host cell is transformed with the vector and cultured. The method of this present invention therefore comprises culturing a suitable cell or cell line, which has been transformed with a DNA sequence coding on expression for a MGPA polypeptide under the control of known regulatory sequences. Regulatory sequences include promoter fragments, terminator fragments and other suitable sequences which direct the expression of the protein in an appropriate host cell. The expressed factor is then recovered, isolated and purified from the culture medium (or from the cell, if expressed intracellularly) by appropriate means known to one of skill in the art.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7):1750–1759 (1985) or Howley et al, U.S. Pat. No. 4,419,446. Other suitable mammalian cell lines, are the monkey COS-1 cell line, and the CV-1 cell line. Further exemplary mammalian host cells include particularly primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, MC1061 and strains used in the following examples) are well-known as host cells in the field of biotechnology. Various strains of *B. subtilis, Pseudomonas,* other bacilli and the like may also be employed in this method.

Many strains of yeast cells known to those skilled in the art are also available as host cells for expression of the polypeptides of the present invention. Additionally, where desired, insect cells may be utilized as host cells in the method of the present invention. See, e.g. Miller et al, *Genetic Engineering,* 8:277–298 (Plenum Press 1986) and references cited therein.

The present invention also provides recombinant molecules or vectors for use in the method of expression of novel MGPA polypeptides. These vectors contain the MGPA DNA sequences and which alone or in combination with other sequences code for MGPA polypeptides of the invention or active fragments thereof. Alternatively, vectors incorporating modified sequences as described above are also embodiments of the present invention and useful in the production of MGPA polypeptides. The vector employed in the method also contains selected regulatory sequences in operative association with the DNA coding sequences of the invention and capable of directing the replication and expression thereof in selected host cells.

One vector which is described in the examples below is pXM, which is particularly desirable for expression in COS cells [Y. C. Yang et al, *Cell,* 47:3–10 (1986)]. Another vector which is desirable for expression in mammalian cells, e.g., CHO cells, and is described in the examples is pEMC2B1. Mammalian cell expression vectors described herein may be synthesized by techniques well known to those skilled in this art. The components of the vectors, e.g. replicons, selection genes, enhancers, promoters, and the like, may be obtained from natural sources or synthesized by known procedures. See, Kaufman et al, *J. Mol. Biol.,* 159:511–521 (1982); and Kaufman, *Proc. Natl. Acad. Sci., USA,* 82:689–693 (1985). Alternatively, the vector DNA may include all or part of the bovine papilloma virus genome [Lusky et al, *Cell,* 36:391–401 (1984)] and be carried in cell lines such as C127 mouse cells as a stable episomal element. The transformation of these vectors into appropriate host cells can result in expression of the MGPA polypeptides.

Other appropriate expression vectors of which numerous types are known in the art for mammalian, insect, yeast, fungal and bacterial expression can also be used for this purpose.

Thus MGPA or active fragments thereof, purified to homogeneity from cell sources or produced recombinantly or synthetically, may be used in a pharmaceutical preparation or formulation to stimulate platelet recovery in patients suffering from thrombocytopenias associated with marrow hypoplasia, e.g., aplastic anemia following chemotherapy or bone marrow transplantation. Other platelet disorders for which treatment with MGPA may be useful include diseases of increased platelet consumption and production, such as, disseminated intravascular coagulation, immune thrombocytopenia, and thrombotic thrombocytopenia. Additionally MGPA may be useful in treating myeloproliferative thrombocytotic diseases, and thrombocytosis in inflammatory conditions and in iron deficiency.

Still another use for MGPA or fragments thereof is in the treatment of disorders resulting from defects in platelets or damage to platelets, e.g. resulting from transient poisoning of platelets by other chemical or pharmaceutical agents or therapeutic manipulations. MGPA may be employed to stimulate the "shedding" of new "undamaged" platelets in such patients.

Therapeutic treatment of such platelet disorders or deficiencies with these MGPA polypeptide compositions may avoid undesirable side effects caused by treatment with presently available serum-derived factors or transfusions of human platelets. It may also be possible to employ one or more peptide fragments of MGPA in such pharmaceutical formulations.

The polypeptides of the present invention may also be employed, alone or in combination with other cytokines, hematopoietins, interleukins, growth factors or antibodies in the treatment of the above-identified conditions.

Therefore, as yet another aspect of the invention are therapeutic compositions for treating the conditions referred to above. Such compositions comprise a therapeutically effective amount of the MGPA polypeptide or a therapeutically effective fragment thereof in admixture with a pharmaceutically acceptable carrier. This composition can be systematically administered parenterally. Alternatively, the composition may be administered intravenously. If desirable, the composition may be administered subcutaneously. When systematically administered, the therapeutic composition for use in this invention is in the form of a pyrogen-free, parenterally acceptable aqueous solution. The preparation of such pharmaceutically acceptable protein solutions, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, the daily regimen should be in the range of 1–1000 micrograms of MGPA protein or fragment thereof or 50 to 5000 units of protein per kilogram of body weight.

The therapeutic method, compositions and polypeptides of the present invention may also be employed, alone or in combination with other cytokines, hematopoietins, interleukins, growth factors or antibodies in the treatment of disease states characterized by other symptoms as well as platelet deficiencies. It is anticipated that this molecule, will prove useful in treating some forms of thrombocytopenia in combination with general stimulators of hematopoiesis, such as IL-3 or GM-CSF. Other megakaryocytic stimulatory factors, e.g., meg-CSF, or other molecules with TPO-like activity may also be employed with MGPA. Additional exemplary cytokines or hematopoietins for such co-administration include G-CSF, CSF-1, IL-1, IL-4, M-CSF, IL-7, or erythropoietin. The dosage recited above would be adjusted to compensate for such additional components in the therapeutic composition. Progress of the treated patient can be monitored by conventional methods.

Other uses for these novel polypeptides are in the development of antibodies generated by standard methods for in vivo or in vitro diagnostic or therapeutic use. Such antibodies may include both monoclonal and polyclonal antibodies, as well as chimeric antibodies or "recombinant" antibodies generated by known techniques. Also provided by this invention are the cell lines generated by presenting MGPA or a fragment thereof as an antigen to a selected mammal, followed by fusing cells of the animal with certain cancer cells to create immortalized cell lines by known techniques. The methods employed to generate such cell lines and antibodies directed against all or portions of a human MGPA polypeptide of the present invention are also encompassed by this invention.

The antibodies of the present invention may be utilized for in vivo and in vitro diagnostic purposes, such as by associating the antibodies with detectable labels or label systems. Alternatively these antibodies may be employed for in vivo and in vitro therapeutic purposes, such as by association with certain toxic or therapeutic compounds or moieties known to those of skill in this art.

The following examples illustratively describe the purification and characteristics of homogeneous human MGPA and other methods and products of the present invention. These examples are for illustration and do not limit the scope of the present invention.

EXAMPLE 1

Radioimmunological Megakaryocyte Growth Promoting Assay

The following assay to detect cell-bound GPIIb/IIIA allows quantitative assessment of in vitro megakaryocytopoiesis. This system uses a radioimmunoassay to measure the generation of megakaryocytes in cultures of normal human bone marrow and is reproducible and reliable as a screen for megakaryocyte growth.

Non-adherent mononuclear bone marrow cells are cultured for two weeks in Iscove's modified Dulbecco's medium, fetal calf serum or other serum or plasma, and other growth factors. Aliquots of cultured cells are washed free of culture media, and exposed to $^{125}$I-HPIID, a murine monoclonal antibody specific to the GPIIb/IIIA complex [see, Grant et al, in "Megakaryocyte Development and Function", eds, Allen R. Liss, pp. 117–121 (1986)]. The binding of iodinated antibody is specific to megakaryocytes, and when free antibody is washed away from the cell pellet, radioactivity bound in the pellet is a quantitative measure of the number of megakaryocytes present.

The quantitative nature of the assay has been demonstrated by correlation with the numbers of morphologically identifiable megakaryocytes in cytospin preparations from individual wells of the MGPA assay. This assay detects small, morphologically difficult-to-recognize megakaryocytes as well as larger, more mature megakaryocytes. Thus it is useful in screening for megakaryocyte growth factors affecting viability, proliferation or maturation at any point in differentiation. This assay cannot distinguish between increases in numbers of cells, increases in size of cells, or increases in the density of GPIIb/IIIA on the cell surface. Therefore, the megakaryocyte morphology and the number and variety of other cells in wells of interest are further evaluated using cytocentrifuge preparations.

This assay correlates well with human megakaryocyte colony assays for response to class I myeloid growth factors (IL-3 and GM CSF), and human aplastic plasma. Optimal growth and maximum signal occurs with $3-4 \times 10^5$ cells per well and an incubation period of 12-14 days. A useful test to confirm or rule out the specificity of individual megakaryocyte growth promoting activities is quantitation of the percent megakaryocytes among cultured cells by immunoalkaline phosphatase stain of GPIIb/IIa expressing cells.

This assay system has readily adapted to the screening of fractionated material for MGPA. For example, after isolation procedures, as described in Example 3, fractions are tested for protein content by absorbtion at $A_{280}$, dialyzed against ammonium bicarbonate buffer (50mM), lyophilized, resuspended in Iscoves medium with 5% fetal calf serum, and filtered through 0.2 micron filters. Each fraction is tested at 3-6 dose levels (dilutions) with two different normal bone marrows with the MGPA assay followed by cytospin analysis and other tests on the marrows, as indicated.

For example, routine screening of a fraction for MGPA is performed using human marrow cultured in 30% fetal calf serum in the presence of synergizing Class I growth factors, usually 5% Phytohemagglutinin-Leukocyte Conditioned Medium (PHALCM) or 10 units of recombinant IL-3 [Genetics Institute, Inc., Cambridge, Mass.] added to support the early stem cells and maximize expression of megakaryocyte specific stimulating activities. Optimal growth for each marrow is assessed in wells supplemented with aplastic plasma and PHALCM, and all wells are assayed in duplicate or triplicate in the radioimmunoassay.

As used throughout this specification, one unit of MGPA is defined as the amount of MGPA required to stimulate megakaryocyte growth to twice that of the background (the fetal calf serum plus PHALCM control) in this assay. Thus, the number of units in a sample equals the difference between the CPM bound at the end of culture in the sample well minus the CPM bound in the fetal calf serum plus PHALCM control, divided by the CPM bound in that same control. The calculation of the number of units in a given fraction is done by averaging the calculated unitage from wells representing the linear part of the dose response curve from two independent experiments using two different marrow samples.

The screening assay system is optimized to detect factors that complete the megakaryocyte developmental program promoted by Class I hemopoietins.

EXAMPLE 2

Isolation of Megakaryocyte Growth Promoting Activity from Plasma

The original isolation of MGPA from citrated plasma from patients with aplastic anemia employed the following purification steps:

(1) Ammonium sulfate precipitation (30-50% pellet, 5 fold purification);

(2) ACA54 or ACA34 gel filtration (10 fold purification);

(3) sulfopropyl sephadex (SPC-50) ion exchange chromatography (in 25 mM ammonium acetate, eluted with sodium chloride, 10 fold purification); and (4) preparative SDS gel electrophoresis (8% polyacrylamide matrix in Laemmli running buffer, 0.01% SDS).

Plasma MGPA was purified through step 3 above 600 times relative to whole aplastic plasma. The apparent MW as determined by the gel filtration and SDS PAGE steps was found to be approximately 40-50 kd.

To establish that the MGPA initially partially purified from aplastic anemia plasma was an activity common to other patients with thrombocytopenia, plasma from four patients with aplastic anemia, four patients with immune thrombocytopenia, three patients with chemotherapy induced thrombocytopenia, two patients with thrombotic thrombocytopenic purpura and one patient with megakaryocytic thrombocytopenia were tested for MGPA.

Each thrombocytopenic plasma yielded maximum bioactivity in the radioimmunological megakaryocyte growth promoting assay of Example 1 in the 30-50% ammonium sulfate precipitate. The molecular weight range of the activity in those fractions further fractionated by gel filtration was consistent. Pooled fractions including relative molecular weights between 30-50 kd from these eight plasmas each showed titratable MGPA.

No titratable MGPA was recovered from similar fractionations of three normal human plasmas, of fetal calf serum, nor of plasma from three patients with thrombocytosis.

EXAMPLE 3

Isolation of MGPA from Urine

MGPA is purified from fresh patient urine using the following sequential fractionation steps: ammonium sulfate precipitation, sulfopropyl sephadex (SPC-50) cation exchange chromatography, polyethyleneimine (PEI) anion exchange membrane filtration, and reverse phase high performance liquid chromatography (HPLC). A summary of this purification scheme is presented in Table I.

The first step employed in the purification is an 80% ammonium sulfate precipitation of protein from unconcentrated urine. The purification of MGPA is one-fold, yielding a fraction with a specific activity of 500 units per milligram protein. When normal human urine is subjected to ammonium sulfate precipitation, MGPA activity in the 80% protein precipitate has approximately 40 units per mg protein. Compared with normal control urine, the level of MGPA present in thrombocytopenic urine is increased by greater than 5-12 fold.

The second purification step is the use of cation exchange column chromatography. The MGPA-containing ammonium sulfate fraction is dialyzed into 25 mM ammonium acetate pH 5.4 and then applied to a sulfopropyl sephadex (SPC-50) ion exchange column equilibrated in the same buffer. Bound protein is eluted in a gradient of NaCl from 0-1M. MGPA elutes at approximately 150 mM NaCl resulting in approximately a 60-fold enrichment of MGPA specific activity.

Further purification of the MGPA is achieved by the third step in which the 150 mM eluate from the SPC-50 column is subjected to anion exchange filtration. MGPA-containing protein is dialyzed into 50 mM ammonium bicarbonate pH 7.4 and passed through a polyethyleneimine (P-I) anion exchange membrane equilibrated in the same buffer. MGPA activity is collected in the flow-through fraction. This step enriches MGPA specific activity by approximately 10-fold.

The fourth step in the purification is achieved using reverse phase high performance liquid chromatography (HPLC) on a C3 column. The PEI membrane filtrate which contains MGPA is dialyzed into 0.05% TFA and loaded onto a C3 column equilibrated in 0.05% TFA. Bound protein is eluted in a gradient of acetonitrile in 0.05% TFA. MGPA elutes between 62 and 70% acetonitrile. At this point in the purification MGPA has a specific activity of greater than $1 \times 10^6$ units per mg protein. Based on SDS polyacrylamide gel electrophoresis (SDS-PAGE), the major protein band at 45,000 under reducing conditions contains the MGPA activity when it is excised from the gel and eluted into a suitable buffer for assay. The purified MGPA obtained from the HPLC step may be suitable for protein sequencing directly or it may be subjected to SDS PAGE prior to protein sequencing to remove minor contaminants which may be present after the fourth step.

TABLE I

Purification of MGPA from Thrombocytopenic Patient Urine

| Purification Step (%) | $^a$Units/mg$^b$ | Total Fold Purification | Total Yield |
|---|---|---|---|
| Ammonium Sulfate precipitation | $5 \times 10^2$ | 1 | 100 |
| SPC-50 | $3 \times 10^4$ | 60 | 13 |
| PEI | $4 \times 10^5$ | 800 | 13 |
| C3 65-70% | $1.1 \times 10^7$ | 22000 | 8 |

$^a$Units are defined as in Example 1.
$^b$Mgs assigned by absorbance at 280 nm.

Urinary MGPA is markedly increased in thrombocytopenic patients. In unfractionated urinary proteins where a mixture of enhancing and inhibitory factors are observed to be present, greater than 5-15 fold more activity in patient urine is observed than in normal human urine. This is strong evidence that the activity measured in the assay of Example 1 is a physiologic regulator of megakaryocyte production that is constitutively produced and measurable in normal urine, but markedly induced and thus measurable in the plasma as well as the urine of thrombocytopenic patients.

EXAMPLE 4

Biological Activities of Human MGPA

The following assays were performed using the purified MGPA from plasma or urine as described. After the first few stages of purification, the biological characteristics of plasma MGPA and urinary MGPA are identical. The recombinant version of the molecule is expected to exhibit the same biological properties in these same assays or other assays (1) The Class I hemopoietins IL3 and GM-CSF maintain viability and support proliferation of undifferentiated myeloid precursor cells and promote megakaryocyte growth in the assay system of Example 1. To demonstrate that MGPA is not IL-3 or GM-CSF, plasma MGPA partially purified by ammonium sulfate precipitation and AcA 34 gel filtration was added to megakaryocyte growth supported by both IL-3 and GMCSF in a dose dependent manner. PHALCM was also employed as a crude source of these activities to provide maximal Class I activity to the cells to be assayed.

Neither IL3 nor GMCSF increase megakaryocyte growth in liquid culture over that of other myeloid cells. Megakaryocyte growth supported by MGPA is not neutralized by antibodies to IL-3 [Genetics Institute] if the culture is supplemented with GM-CSF to support stem cell growth. Similarly, megakaryocyte growth supported by MGPA is not neutralized by antibodies to GM-CSF if IL-3 is supplied. A combination of these antisera reverses all megakaryocyte growth stimulated by PHALCM. Human bone marrow grown in the presence of IL3 and GMCSF produced similar amounts of megakaryocytes in the presence or absence of antiserum against GMCSF. When human marrow was grown in methylcellulose, very few granulocyte/macrophage colonies are stimulated above FCS control with 3 units/ml of partially purified MGPA.

MGPA adds to the effect of PHALCM in the marrow cultures. On day 14 of culture very little dose dependent megakaryocyte growth is seen in cultures supplemented with FCS and HPLC-purified MGPA as the only exogenous growth factors. Marked dose dependent enhancement of megakaryocyte growth by MGPA is observed in the presence of PHALCM, IL-3, and GM-CSF. Each of these sources of class I hemopoietins appears to support the same or very similar groups of MGPA responsive cells, as the response curves are quite similar from most marrows.

Based on these results it is expected that MGPA will produce an additive or synergistic effect with either IL3 and/or GM-CSF in therapeutic applications.

(2) That MGPA stimulates megakaryocyte growth has also been shown by testing MGPA in the human megakaryocyte colony assays of Mazur et al, Blood, 57:277-286 (1981) and Solberg et al, in The Inhibitors of Hematopoiesis, pp. 111-121 (1987). MGPA alone fails to support megakaryocyte colony growth from either human marrow or peripheral blood in these systems. MGPA markedly increases the number of megakaryocyte colonies supported by IL-3, consistent with the concept that MGPA acts to complete the differentiation supported by IL-3.

(3) Similarly in murine systems, MGPA promoted megakaryocyte maturation in the serum-free Acetylcholinesterase assay of Burstein, cited above.

(4) MGPA only supported murine megakaryocyte colony formation in the presence of IL-3 or WEHI conditioned medium in a megakaryocyte colony assay using murine bone marrow in a fibrin clot [S. Kuriya et al, Exp. Hematol., 15:896-901 (1987)].

(5) Cytospin preparations of MGPA supported cultures confirmed that MGPA not only increases the growth of megakaryocytes but also increases the number of megakaryocytes relative to other cells, as would be found with a specific promoter of megakaryocyte growth. To test for this, partially purified MGPA from SPC-50 was titrated in FCS, alone, or in 5% PHALCM. The percent megakaryocytes was determined on cytospin preparations of cells from the liquid marrow cultures using an immunoalkaline phosphatase stain with antibody against GPIIb/IIIa. 1000 cells were counted on each slide. At each dose of MGPA tested, the percent of megakaryocytes correlated well with the total CPM bound in the assay of Example 1. When the MGPA plus PHALCM treated culture, the IL-3 treated culture and GM-CSF treated culture are compared within the optimal dose range for MGPA, the actual percentage of megakaryocytes decreases in both the IL-3 and GM-CSF treated samples at higher concentrations due to an increase in number of other myeloid cells that grow in response to these factors.

The megakaryocytes supported by MGPA in culture are consistently more mature and somewhat larger in size than those grown in control wells (FCS with PHA-LCM) suggestive of a maturational effect. Marrow supported by FCS and PHA-LCM has produced recognizable megakaryocytes ranging in stage from I to II-/III to IV. A cytospin from the same marrow grown under identical conditions except that HPLC-purified MGPA was added show that not only are more megakaryocytes recognizable per field, but they tend to be more mature and have far denser cytoplasm. No increase is seen in the number of other myeloid cells.

(6) The following tests for stability were performed on both urinary and plasma purified MGPA and have revealed the following characteristics of MGPA. MGPA is stable to boiling, to guanidine hydrochloride treatment, to O-glycanase treatment; to digestion with trypsin; and to multiple cycles of lyophilization or freeze thawing.

EXAMPLE 5

Amino Acid Sequence and Cloning of MGPA

Pure MGPA is sequenced using conventional microsequencing techniques suitable for studies of picomolar amounts of protein. Amino terminal sequence is complemented with sequences of peptides derived by peptidase or cyanogen bromide digestion, separated by reverse phase HPLC or SDS gel electrophoresis and electroelution. The amino acid sequence of MGPA is screened for uniqueness using the PIR data banks.

The degree of glycosylation is assessed by amino acid/amino sugar determination and by molecular weight shift on SDS gel of iodinated MGPA after digestion by a panel of glycosidases including neuraminidase, sialidase, F-endoglycosidase, and G-endoglycosidase.

The generation of large amounts of MGPA for extensive physical, chemical, cell biological and preclinical studies is optimally performed by molecular cloning of the MGPA gene and expression of this gene or corresponding cDNA in any one of a variety of host/vector systems.

To obtain the cDNA for MGPA, probes consisting of pools of oligonucleotides or unique oligonucleotides are designed from the tryptic sequences according to the method of R. Lathe, *J. Mol. Biol.*, 183(1):1-12 (1985). The oligonucleotide probes are synthesized on an automated DNA synthesizer.

Because the genetic code is degenerate (more than one codon can code for the same amino acid) a mixture of oligonucleotides are synthesized that contain all possible nucleotide sequences encoding the amino acid sequence of the selected tryptic fragment or portion thereof. It may be possible in some cases to reduce the number of oligonucleotides in the probe mixture based on codon usage because some codons are rarely used in eukaryotic genes, and because of the relative infrequency of the dinucleotide CpG in eukaryotic coding sequences [see J. J. Toole et al, *Nature*, 312:342-347 (1984)]. The regions of the amino acid sequences used for probe design are chosen by avoiding highly degenerate codons where possible. The oligonucleotides are synthesized on an automated DNA synthesizer and the probes are then radioactively labelled with polynucleotide kinase and $^{32}$p-ATP.

cDNA is then synthesized from polyadenylated RNA from a human cell line, e.g., one of the above mentioned cell sources of MGPA using either conventional cloning technology or polymerase chain reaction technology. The cDNA library may be cloned into lambda ZAP [Stratagene Cloning Systems, La Jolla, CA] or other suitable vectors using established techniques Calif. (see Toole et al cited above). Recombinants from this library are plated and duplicate nitrocellulose replicas made of the plates. The oligonucleotides are kinased with $^{32}$P gamma ATP and hybridized to the replicas at a temperature predicted from the length and base composition of the probes [See, J. Singer-Sam et al, *Proc. Nat'l. Acad. Sci. USA.* 80:802-806 (1983) and S. V. Suggs et al, in "Developmental Biology Using Purified Genes", ICN-UCLA Symposium on Molecular and Cellular Biology, eds. Brown D. D. and Fox, C. F. (Academic, N.Y.), Vol. 23, pp. 683-693 (1981)] in standard hybridization solution overnight. The filters are then washed in 0.5XSSC at the same temperature until the background radioactivity is lowered to an acceptable level to allow autoradiography. Alternatively, the hybridization and washes may be performed in the presence of tetraalkylammonium salt solution [See K. A. Jacobs et al, *Nucl. Acids Res.*, 16:4637-4650 (1988)]. Duplicate positives are plaque purified.

A complete or partial cDNA sequence is obtained by this method. This sequence may be used optionally as a probe to rescreen the library to obtain full length cDNAs. It is also possible that partial cDNAs may yield an active MGPA fragment.

Alternatively, the MGPA gene may be isolated from a human genomic library (available from Stratagene) in λ Zap using the oligonucleotide hybridization probes described above. The genomic MGPA clone is expressed directly in mammalian cells or used to isolate a cDNA. In the latter case, the MGPA gene is used as a hybridization probe to identify a source of MGPA in RNA. Alternatively, the MGPA gene is expressed transiently in COS1 cells to generate an MGPA mRNA that can be used to generate a cDNA.

EXAMPLE 6

Expression of Recombinant Human MGPA

To produce MGPA or an active fragment thereof, the cDNA encoding it is transferred into an appropriate expression vector, of which numerous types are known in the art for human, insect, yeast, fungal and bacterial expression, by standard molecular biology techniques.

One such vector for mammalian cells is pXM [Y. C. Yang et al, *Cell*, 47:3-10 (1986)]. This vector contains the SV40 origin of replication and enhancer, the adenovirus major late promoter, a cDNA copy of the adenovirus tripartite leader sequence, a small hybrid intervening sequence, an SV40 polyadenylation signal and the adenovirus VA I gene, in appropriate relationships to direct the high level expression of the desired cDNA in mammalian cells [See, e.g., Kaufman, *Proc. Natl. Acad. Sci. USA*, 82:689-693 (1985)]. The pXM vector is linearized with the endonuclease enzyme XhoI and subsequently ligated in equimolar amount separately to the cDNA encoding MGPA that has been previously modified by addition of synthetic oligonucleotides that generate Xho I complementary ends to generate constructs for expression.

Another vector for mammalian expression is pEMC2B1. This vector may be derived from pMT2pc which has been deposited with the American Type Culture Collection (ATCC), Rockville, Md. (USA) under Accession Number ATCC 40348. The DNA is linearized by digestion of the plasmid with PstI. The DNA is then blunted using T$_4$ DNA polymerase. An oligonucleotide 5' TGCAGGCGAGCCT-GAATTCCTCGA 3' is then ligated into the DNA, recreating the PstI site at the 5' end and adding an EcoRI site and XhoI site before the ATG of the DHFR cDNA. This plasmid is called pMT21. pMT21 is cut with EcoRI and XhoI which cleaves the plasmid at two adjacent cloning sites. An EMCV fragment of 508 base pairs is cut from pMT$_2$ECAT$_1$ [S. K. Jong et al, *J. Virol.*, 63:1651-1660 (1989)] with the restriction enzymes EcoRI and TaqαI. A pair of oligonucleotides 68 nucleotides in length are synthesized to duplicate the EMCV sequence up to the ATG. The ATG is changed to an ATT, and a C is added, creating a XhoI site at the 3' end. A TaqαI site is situated at the 5' end. The sequences of the oligonucleotides are: 5' CGAGGT-TAAAAAACGTCTAGGCCCCCCGAACCACGG-GGACGTGGTTTTCCTTT GAAAACAC-GATTGC 3' and its complementary strand.

Ligation of the pMT21 EcoRI-to-XhoI fragment to the EMCV EcoRI-to-TaqoI fragment and to the TaqoI/XhoI oligonucleotides produces the vector pEMC2B1. This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells. The EMC2B1 vector is linearized with the endonuclease enzyme EcoRI and subsequently ligated in equimolar amount separately to the cDNA encoding MGPA that has been previously modified by addition of synthetic oligonucleotides that generate EcoRI complementary ends to generate constructs for expression. These constructs can be expressed in various hosts with appropriate vectors.

The vector is then introduced into appropriate host cells by conventional genetic engineering techniques. The transformed cells are cultured and the expressed MGPA is recovered and purified from the culture medium using standard techniques.

a. Mammalian Cell Expression

To obtain expression of the MGPA protein, the pXM construct containing the cDNA is mixed and transfected into COS cells, for example. The conditioned medium from the transfected COS cells contains MGPA biological activity as measured in the megakaryocyte growth promoting assay of Example 1.

The mammalian cell expression vectors described herein may be synthesized by techniques well known to those skilled in this art. One skilled in the art can also construct other mammalian expression vectors comparable to the pXM vector by, e.g., inserting the DNA sequence of the MGPA from the plasmid with appropriate enzymes and employing well-known recombinant genetic engineering techniques and other known vectors, such as pJL3 and pJL4 [Gough et al., *EMBO J.*, 4:645-653 (1985)] and pMT2 (starting with pMT2-VWF, ATCC #67122; see PCT application PCT/US87/00033).

Mammalian host cells other than COS cells may also be employed in MGPA expression. For example, preferably for stable integration of the vector DNA, and for subsequent amplification of the integrated vector DNA, both by conventional methods, CHO cells may be employed as a mammalian host cell of choice.

Once the vectors and host cells are selected and transformed, stable transformants are then screened for expression of the product by standard immunological, biological or enzymatic assays, such as those described above in Examples 1 and 4. The presence of the DNA and mRNA encoding the MGPA polypeptides may be detected by standard procedures such as Southern and Northern blotting. Transient expression of the DNA encoding the polypeptides during the several days after introduction of the expression vector DNA into suitable host cells is measured without selection by bioactivity or immunologic assay of the proteins in the culture medium.

b. Bacterial Exoression Systems

Similarly, one skilled in the art could manipulate the sequences encoding the MGPA polypeptide by eliminating any human regulatory sequences flanking the coding sequences and inserting bacterial regulatory sequences to create bacterial vectors for intracellular or extracellular expression of the MGPA polypeptide of the invention by bacterial cells. The DNA encoding the polypeptides may be further modified to contain different codons to optimize bacterial expression as is known in the art. Preferably the sequences encoding the mature MGPA are operatively linked in-frame to nucleotide sequences encoding a secretory leader polypeptide permitting bacterial expression, secretion and processing of the mature MGPA polypeptides, also by methods known in the art. The expression of MGPA in E. coli using such secretion systems is expected to result in the secretion of the active polypeptide. This approach has yielded active chimeric antibody fragments [See, e.g., Bitter et al, *Science,* 240:1041-1043 (1983)]. Alternatively, the MGPA may be expressed as a cytoplasmic protein in *E. coli.* In this case, the molecule would most likely have to be refolded after complete denaturation with guanidine hydrochloride, a process also known in the art. For procedures for isolation and refolding of intracellularly expressed proteins, see, for example, U.S. Pat. No. 4,512,922.

The compounds expressed through either route in bacterial host cells may then be recovered, purified, and/or characterized with respect to physicochemical, biochemical and/or clinical parameters, all by known methods.

c. Insect or Yeast Cell Expression

Similar manipulations can be performed for the construction of an insect vector for expression of MGPA polypeptides in insect cells [See, e.g., procedures described in published European patent application 155,476].

Similarly yeast vectors are constructed employing yeast regulatory sequences to express cDNA encoding the precursor, in yeast cells to yield secreted extracellular active MGPA. Alternatively the polypeptide may be expressed intracellularly in yeast, the polypeptide isolated and refolded to yield active MGPA. [See, e.g., procedures described in published PCT application WO 86/00639 and European patent application EP 123,289. ]

EXAMPLE 7

Construction of CHO Cell Lines Expressing High Levels of MGPA

One method for producing high levels of the MGPA polypeptide of the invention from mammalian cells involves the construction of cells containing multiple copies of the cDNA encoding the MGPA.

The cDNA is co-transfected with an amplifiable marker, e.g., the DHFR gene for which cells containing increasing concentrations of methotrexate (MTX) according to the procedures of Kaufman and Sharp, *J. Mol. Biol.*, (1982) supra. This approach can be employed with a number of different cell types.

For example, the pXM vector or the pEMC2B1 vector containing the MGPA gene in operative association with other plasmid sequences enabling expression thereof is introduced into DHER-deficient CHO cells, DUKX-BII, along with a DHFR expression plasmid such as pAdD26SVpA3 [Kaufman, *Proc. Natl. Acad. Sci. USA.* 82:689-693 (1985)] by either calcium phosphate coprecipitation or protoplast fusion, followed by transfection. The MGPA gene and marker gene may be on a single plasmid or on two plasmids for transfection. DHFR expressing transformants are selected for growth in alpha media with dialyzed fetal calf serum. Transformants are checked for expression of MGPA by bioassay, immunoassay or RNA blotting and positive pools are subsequently selected for amplification by growth in increasing concentrations of MTX (sequential steps in 0.02, 0.2, 1.0 and 5 uM MTX) as described in Kaufman et al., *Mol. Cell Biol.*, 5:1750 (1983). The amplified lines are cloned, and MGPA expression is monitored by the MGPA assay of Example I. MGPA expression is expected to increase with increasing levels of MTX resistance.

In any of the expression systems described above, the resulting cell lines can be further amplified by appropriate drug selection, resulting cell lines recloned and the level of expression assessed using the MGPA assay described in Example I.

The MGPA expressing CHO cell lines can be adapted to growth in serum-free medium. Homogeneous MGPA can be isolated from conditioned medium from the cell line using methods familiar in the art, including techniques such as lectin-affinity chromatography, reverse phase HPLC, FPLC and the like.

EXAMPLE 8

Antibodies to MGPA

Purified MGPA and synthesized peptides from its sequence will be used to produce polyclonal antisera in rabbits and monoclonal antibodies in mice using conventional methods to generate ahtibodies to detect and quantitate MGPA in clinical samples, and to screen for antibodies that block MGPA for therapeutic use.

Mice and rabbits are immunized with pure urinary MGPA or with individual peptide sequences 12-20 amino acids in length. Serum from the animals is collected weekly and tested for reactivity by Western blotting to whole MGPA. Wells with immunoreactivity on Western blot are expanded and subcloned. Individual antibodies are tested for their affinity to MGPA, and for their ability to block the action of MGPA by the direct addition of supernatant to marrow cell cultures where both polyclonal rabbit antisera [anti-IL-3, anti-GM-CSF] and monoclonal murine antisera [anti-erythropoietin] block the effect of relevant growth factors.

These monoclonal and polyclonal antibodies are used in radioimmunoassays for evaluation of patient samples. Measurement of 0.5-500 units/ml should be easily performed in plasma or urine (timed out-put) with monoclonals of average affinity.

A series of antibodies to MGPA is useful in detecting and blocking MGPA, and determining its receptor binding site. Both polyclonal antisera and a series of monoclonals against MGPA peptides are useful in establishing the immunologic identity of plasma and urinary MGPA.

The foregoing description details presently preferred embodiments of the invention. Numerous modifications and variations in practice of this invention are expected to occur to those skilled in the art. Such modifications and variations are encompassed within the following claims.

What is claimed is:

1. Isolated megakaryocyte growth promoting activity (MGPA) protein having the following characteristics:
   (1) an apparent molecular weight of approximately 40-50 kD as determined by SDS-PAGE;
   (2) a specific activity in a radioimmunological megakaryocyte growth promoting assay of approximately $1 \times 10^6$ to $1.1 \times 10^7$ units per mg polypeptide; and
   (3) an ability to support megakaryocyte colony growth in a human bone marrow liquid culture assay in the presence of IL-3.

2. Isolated megakaryocyte growth promoting (MGPA) activity protein having the following characteristics:
   (1) an apparent molecular weight of approximately 40-50 kD as determined by SDA-PAGE;
   (2) a specific activity in a radioimmunological megakaryocyte growth promoting assay of greater than $1 \times 10^6$ units per mg polypeptide; and
   (3) an ability to support megakaryocyte growth in a human bone marrow liquid culture assay in the presence of IL-3.

3. The protein according to claim 2 having one or more of the following characteristics:
   (1) an apparent molecular weight of approximately 45 kd as determined by sodium dodecyl sulfate polyacrylamide gel electrophoresis;
   (2) an apparent molecular weight of approximately 40-50 kd as determined by gel filtration chromatography;
   (3) the inability to bind to Wheat Germlectin;
   (4) the ability to bind to a Pharmacia Mono S cation exchange column at acidic pH;
   (5) the inability to bind to an anion exchange resin at neutral pH;
   (6) presence in 30-50% ammonium sulphate precipitate of thrombocytopenic patient plasma.

4. The protein according to claim 2 produced by culturing a cell line transformed with a DNA sequence encoding expression of MGPA in operative association with an expression control sequence therefor.

5. A composition comprising the MGPA of claim 2 in a pharmaceutically effective vehicle.

6. The composition according to claim 5 further comprising a cytokine, hematopoietin, growth factor, meg-CSF or thrombopoietin-like factor.

7. The composition according to claim 6 where said cytokine is selected from the group consisting of G-CSF, CSF-1, GM-CSF, IL-1, IL-3, IL-4, meg-CSF, erythropoietin, IL-6, TPO, M-CSF and IL-7.

8. The composition according to claim 7 wherein said cytokine is IL-3 and GM-CSF.

* * * * *